United States Patent
Bishop et al.

(10) Patent No.: US 9,619,460 B2
(45) Date of Patent: *Apr. 11, 2017

(54) IDENTIFYING WORD-SENSES BASED ON LINGUISTIC VARIATIONS

(71) Applicant: International Business Machines Corporation, Armonk, NY (US)

(72) Inventors: Timothy A. Bishop, Minneapolis, MN (US); Stephen A. Boxwell, Columbus, OH (US); Benjamin L. Brumfield, Cedar Park, TX (US); Nirav P. Desai, Austin, TX (US); Stanley J. Vernier, Grove City, OH (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/273,739

(22) Filed: Sep. 23, 2016

(65) Prior Publication Data

US 2017/0004130 A1    Jan. 5, 2017

Related U.S. Application Data

(63) Continuation of application No. 15/263,530, filed on Sep. 13, 2016, which is a continuation of application No. 15/070,463, filed on Mar. 15, 2016, now Pat. No. 9,442,919, which is a continuation of application No. 14/621,614, filed on Feb. 13, 2015.

(51) Int. Cl.
    *G06F 17/27*    (2006.01)

(52) U.S. Cl.
    CPC ........ *G06F 17/2785* (2013.01); *G06F 17/277* (2013.01); *G06F 17/2775* (2013.01)

(58) Field of Classification Search
    CPC . G10L 15/183; G10L 15/22; G06F 17/30854; G06F 17/30696; G06F 17/277; G06F 17/2785; G06F 17/30554; G06F 17/20684; G06F 17/271; G06F 17/274; G06F 17/28; G06F 17/30539
    USPC .......... 704/9, 10, 257, 3; 707/706, 707, 708, 707/723, 737, 999.003, 999.101; 709/230; 715/230
    See application file for complete search history.

(56) References Cited

U.S. PATENT DOCUMENTS

| | | |
|---|---|---|
| 5,794,050 A | 8/1998 | Dahlgren et al. |
| 6,139,201 A | 10/2000 | Carbonell et al. |
| 7,814,105 B2 | 10/2010 | Knepper et al. |

(Continued)

OTHER PUBLICATIONS

Pending U.S. Appl. No. 15/263,530, filed Sep. 13, 2016, entitled: "Identifying Word-Senses Based on Linguistic Variations", 30 pages.

(Continued)

*Primary Examiner* — Vijay B Chawan
(74) *Attorney, Agent, or Firm* — L. Jeffrey Kelly

(57) ABSTRACT

One or more words are received. A set of frequency of occurrence values of the received word(s) within a set of domain tables is determined. A domain table in the set of domain tables is associated to the received word(s), based on the set of frequency of occurrence values meeting a threshold value. A word-sense of the received word(s) is determined based on a corresponding word-sense in the associated domain table and/or corresponding domain dictionary.

1 Claim, 5 Drawing Sheets

(56) References Cited

U.S. PATENT DOCUMENTS

| | | | |
|---|---|---|---|
| 8,145,677 B2* | 3/2012 | Al-Shameri | G06F 17/30333 707/802 |
| 8,180,783 B1* | 5/2012 | Fletcher | G06F 17/30684 707/723 |
| 8,478,581 B2 | 7/2013 | Chen | |
| 8,625,925 B2* | 1/2014 | Kokemohr | G06F 3/04845 382/274 |
| 8,788,289 B2 | 7/2014 | Flanagan et al. | |
| 8,812,292 B2 | 8/2014 | Ceusters et al. | |
| 9,223,836 B1* | 12/2015 | Fletcher | G06F 17/30684 |
| 9,442,919 B2* | 9/2016 | Bishop | G06F 17/2785 |
| 2006/0117052 A1* | 6/2006 | Bradford | G06F 17/2785 |
| 2007/0073894 A1* | 3/2007 | Erickson | G06F 17/30864 709/230 |
| 2007/0106499 A1 | 5/2007 | Dahlgren et al. | |
| 2007/0106657 A1 | 5/2007 | Brzeski et al. | |
| 2007/0213985 A1* | 9/2007 | Corwin | G10L 15/22 704/257 |
| 2009/0132233 A1* | 5/2009 | Etzioni | G06F 17/28 704/3 |
| 2009/0254572 A1 | 10/2009 | Redlich et al. | |
| 2010/0131563 A1* | 5/2010 | Yin | G06F 17/3071 707/794 |
| 2010/0223276 A1 | 9/2010 | Al-Shameri et al. | |
| 2010/0235313 A1* | 9/2010 | Rea | G06F 17/30265 706/52 |
| 2011/0246486 A1* | 10/2011 | Peng | G06F 17/2775 707/750 |
| 2012/0290577 A1* | 11/2012 | Cai | G06F 17/30256 707/737 |
| 2016/0239482 A1 | 8/2016 | Bishop et al. | |

OTHER PUBLICATIONS

IBM: List of IBM Patents or Patent Applications Treated As Related (Appendix P), Dated Nov. 10, 2016, 2 pages.

* cited by examiner

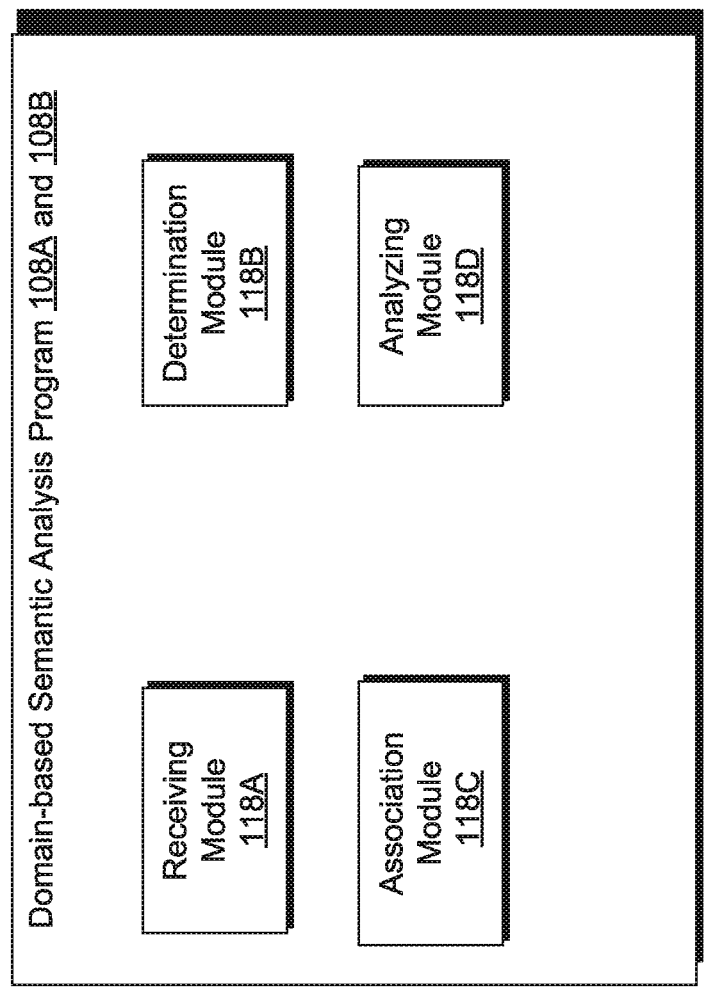

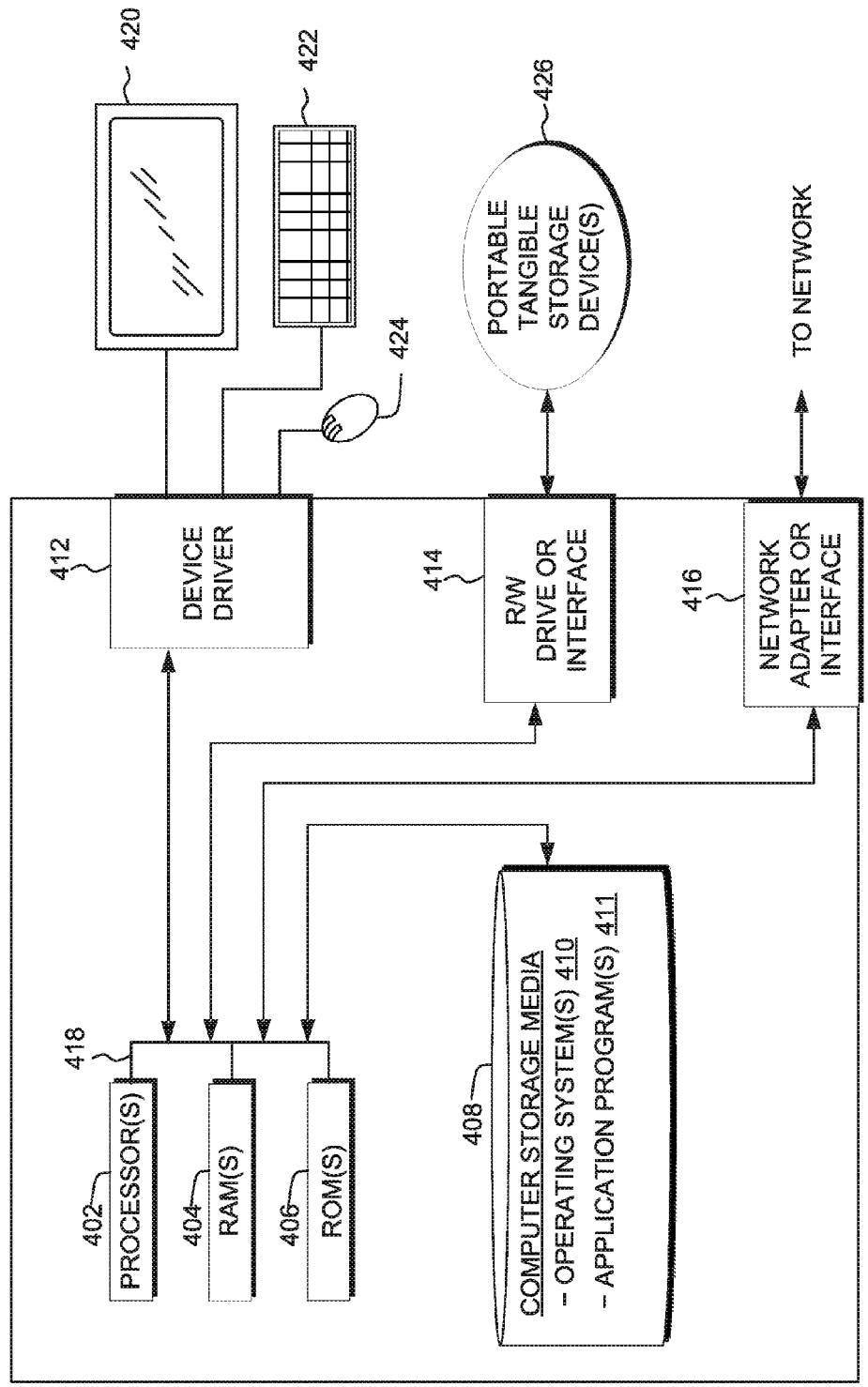

IDENTIFYING WORD-SENSES BASED ON LINGUISTIC VARIATIONS

FIELD OF INVENTION

The present invention relates generally to the field of computer systems, and more particularly to semantic analysis.

BACKGROUND

Use and meaning of a particular word or a phrase vary by several factors. Currently, several semantic analysis techniques use syntactic features and consider the semantic context of a given word to identify its word-sense using various statistical and supervised/semi-supervised machine learning techniques. However, none of these techniques consider domain-specific factors such as temporal, regional, cultural, and colloquial language variations; this could result in obtaining the wrong word-sense of a particular word or a phrase.

SUMMARY

It may be desirable to implement a method, system, and computer program product which considers various aspects of use of a particular word in order to correctly semantically analyze a received word and determine the correct word-sense.

An embodiment of the present disclosure provides a method for analyzing a word with respect to temporal, cultural, region-specific, linguistic, and other variances in order to obtain an accurate word-sense of a received word. The method receives a word for evaluation and determines the frequency of occurrence and/or the frequency of co-occurrence of the received word within one or more domain tables. A domain table is an array of statistical information about words and corresponding word-senses generated based on word frequency in a corpus, word co-occurrence in a corpus, and/or domain-specific dictionaries. The method associates domain table(s) to the received word based on frequency of occurrence and/or frequency of co-occurrence of the received word within the domain tables and determines a word-sense for the received word based on a corresponding word-sense in the associated domain table(s) and/or a corresponding domain dictionary.

According to a further embodiment, a system for analyzing a word with respect to temporal, cultural, region-specific, linguistic, and other variances in order to obtain an accurate word-sense of a received word is provided. The system receives a word for evaluation and determines the frequency of occurrence and/or the frequency of co-occurrence of the received word within one or more domain tables. The system associates domain table(s) to the received word based on frequency of occurrence and/or frequency of co-occurrence of the received word within the domain tables and determines a word-sense for the received word based on a corresponding word-sense in the associated domain table(s) and/or a corresponding domain dictionary.

According to another embodiment, a computer program product for analyzing a word with respect to temporal, cultural, region-specific, linguistic, and other variances in order to obtain an accurate word-sense of a received word is provided. The computer program product receives a word for evaluation and determines the frequency of occurrence and/or the frequency of co-occurrence of the received word within one or more domain tables. The computer program product associates domain table(s) to the received word based on frequency of occurrence and/or frequency of co-occurrence of the received word within the domain tables and determines a word-sense for the received word based on a corresponding word-sense in the associated domain table(s) and/or a corresponding domain dictionary.

BRIEF DESCRIPTION OF THE SEVERAL VIEWS OF THE DRAWINGS

FIGS. 1A-B are schematic block diagrams depicting an exemplary computing environment for a Domain-based Semantic Analysis Program, according to an aspect of the present invention.

FIG. 4 is a block diagram of internal and external components of computers and servers depicted in FIG. 1 according an embodiment of the present invention.

DETAILED DESCRIPTION

Figure 1A:
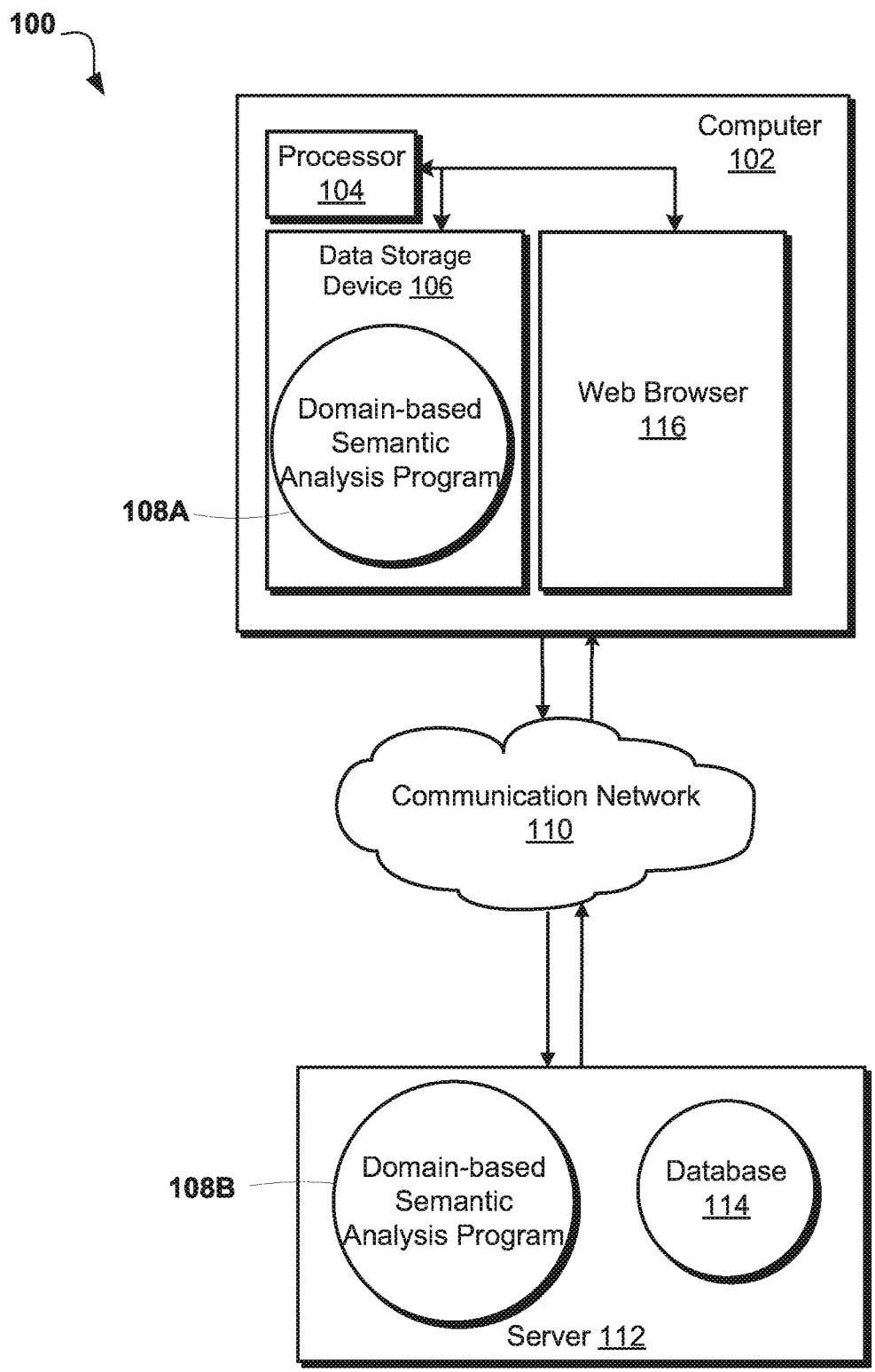

While the present invention is particularly shown and described with respect to preferred embodiments thereof, it will be understood by those skilled in the art that changes in forms and details may be made without departing from the spirit and scope of the present application. It is therefore intended that the present invention not be limited to the exact forms and details described and illustrated herein, but falls within the scope of the appended claims.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1A is a schematic block diagram depicting an exemplary computing environment 100 for domain-based semantic analysis. In various embodiments of the present invention computing environment 100 includes a computer 102 and server 112 connected over communication network 110.

Computer 102 may include with a processor 104 and a data storage device 106 that is enabled to run a Domain-based Semantic Analysis Program 108A and a web browser 116 in order to display the result of a program on server 112 such as Domain-based Analysis Program 108B communicated by communication network 110. Non-limiting examples of a web browser may include: Firefox®, Explorer®, or any other web browser. All brand names and/or trademarks used herein are the property of their respective owners.

Computing environment 100 may also include a server 112 with a database 114. The server 112 may be enabled to run a Domain-based Semantic Analysis Program 108B. Communication network 110 may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. communication network 110 may also include a number of different types of networks, such as, for example, an intranet, a local area network (LAN), or a wide area network (WAN).

It should be appreciated that FIG. 1A provides only an illustration of one implementation and does not imply any limitations with regard to the environments in which different embodiments may be implemented. Many modifications to the depicted environments may be made based on design and implementation requirements.

The computer 102 may communicate with server 112 via the communication network 110. The communication network 110 may include connections, such as wire, wireless communication links, or fiber optic cables.

Computer 102 and server 112 may be, for example, a mobile device, a telephone, a personal digital assistant, a netbook, a laptop computer, a tablet computer, a desktop computer, or any type of computing device capable of running a program and accessing a network. A program, such as a Domain-based Semantic Analysis Program 108A and 108B may run on the client computer 102 or on the server 112.

Referring now to FIG. 1B, the components of the Domain-based Semantic Analysis Program 108A and 108B, are illustrated. Domain-based Semantic Analysis Program 108A and 108B may include a receiving module 118A, determination module 118B, association module 118C, and analyzing module 118D. Receiving module 118A may receive one or more digital text streams, such as one or more words. Determination module 118B may determine the frequency of occurrence of the received word(s) within a set of one or more domain tables. Association module 118C may associate one or more domain tables (from the set of one or more domain tables) with the received word(s). Analyzing module 118D may semantically analyze the received word(s) based the associated domain tables and corresponding domain specific word-sense dictionaries.

Figure 2:
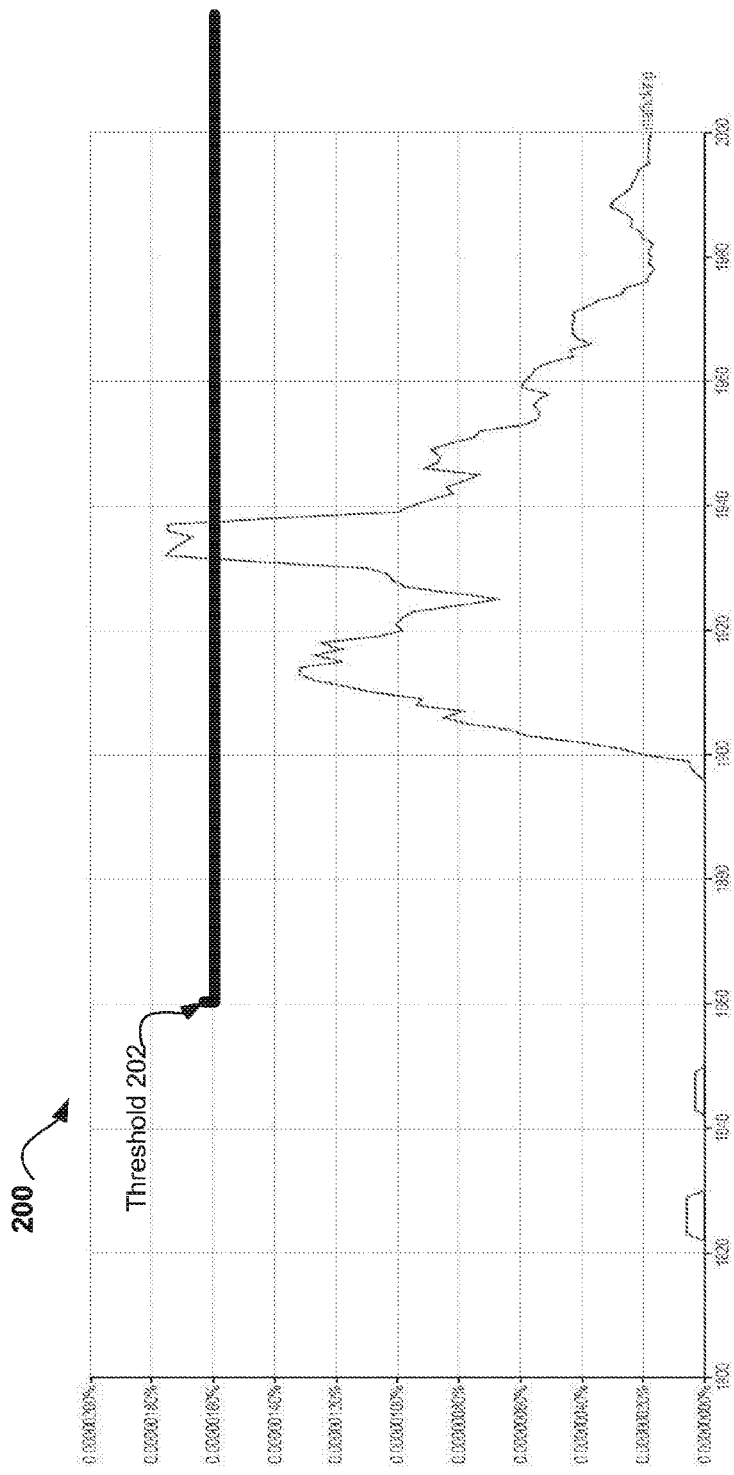
FIG. 2 is schematic block diagram depicting a graphical representation of content of a domain table and a threshold value according to an embodiment of the present invention.

FIG. 2 is a schematic block diagram depicting a graphical representation of content of a domain table and operation of association module 118C with respect to a threshold value according to an embodiment of the present invention. In this embodiment, content of a "temporal frequency of occurrence" domain table for the word mafficking and operation of association module 118C with respect to a threshold value are depicted. Environment 200 is a graphical representation of the content of the above-mentioned domain table and threshold.

A domain table comprises one or more arrays of aggregated statistical information about words, within a particular domain, and one or more of corresponding word-senses and temporal properties. Non-limiting examples of the information about words may be frequency of usage, frequency of occurrence, frequency of co-occurrence with other words, year of usage, or usage within a specific profession or domain, or context of usage. Profession, for the purposes of the present disclosure is a vocation or business requiring knowledge of science or traditional business dealings. Non-limiting examples of a profession is medical, legal, paleontological, accounting, or engineering.

Non-limiting examples of a domain table comprise a table of frequency of usage of words and their corresponding word-senses within a profession such as the medical profession (e.g. Profession Frequency of Occurrence Domain Table such as Medical/Legal/paleontology/ . . . Frequency of Occurrence Domain Table); a table of a frequency of usage of multiple words and their corresponding word-senses when those words have co-occurred within the same sentence or a corpus within the context of a profession such as the legal profession (e.g. Profession Frequency of Co-Occurrence Domain Table such as Legal/Medical/Paleontology/ . . . Frequency of Co-Occurrence Domain Table); or a table of a frequency of usage of words and their corresponding word-senses during a specific time period (e.g. Temporal Frequency of Occurrence Domain Table).

A domain table may be based on any language variation, therefore, domain table(s) are not limited to profession-specific word-senses and may pertain to, among other things, colloquial, cultural, or regional language variations and word-senses. For example, a colloquial domain table may be aggregated statistical data regarding words specific to colloquial use and their corresponding word-sense (e.g. "kicks" and its corresponding word-sense "shoes"); a cultural or regional language domain table may be a table of data on different usage and word-senses for the same word or meaning (e.g. the phrase "fixing" has a word-sense of "about to" or "that the action described is in the very near future" in some southern states in particular Texas, however in some northern states is has a word-sense of "repair" or "fasten securely in a particular place or position").

It should be appreciated that arrangement of array(s) of aggregated statistical information may comprise statistical information of both temporal properties and word-senses. For example, a domain table may include frequency of occurrence of medical words and their corresponding word-senses during the $18^{th}$ century. In one example, the domain table(s) may be generated by comparing usage of terms, their corresponding word-senses and frequencies in various literature. For example, a domain table may be generated based on a term frequency chart generated by an n-gram viewer. An n-gram viewer is a phrase-usage graphing tool which charts the count of selected n-gram as found in million books digitized by different companies. An n-gram is a sequence of letters of any length, which could be a word, a misspelling, or a phrase.

In this embodiment, content of a "temporal frequency of usage of mafficking" domain table is illustrated utilizing a graph which comprises X and Y axes. This domain table comprises a set of aggregated statistical information about frequency of usage of the word mafficking and the corresponding year of usage. In this embodiment, the X-axis represents chronology (e.g. increments of time, and in this case increments of 20 years), and the Y-axis represents the frequency of use. The Y-axis illustrates the percentage of usage of the word mafficking within a variety of corpuses in a particular 20-year increment of time by performing statistical analysis on unigrams generated from Google Books n-gram Viewer. Any given coordinate on the graph represents the usage of the word mafficking and the year of said usage. For example, using this domain table, one can determine that in 1895, the word mafficking was used 0%, in 1935 the usage was nearly 0.0000016705%, or in 1945=0.0000007370%. As explained below in FIGS. 3 and 4, these values are used by determination module 118B in order to calculate the frequency of usage (see below).

In this embodiment, operation of association module 118C and in particular the use of a threshold value by association module 118C is depicted. As explained thoroughly below in FIGS. 3 and 4, association module 118C may use the threshold value in order to associate a received word with a domain table. Association module 118C may associate a domain table with a received word if the frequency of occurrence of the word satisfies a threshold value within the domain table (see below).

In this embodiment, threshold value 202 is set at 0.00000160%. Association module 118C may use threshold value 202 to associate the temporal frequency of use of mafficking domain table with the word mafficking. Association module 118C determines whether, within this domain table, the word mafficking has been used at a higher value than the threshold value 202 for a particular temporal increment. In this embodiment, the usage value for mafficking is higher than threshold value 202 at a temporal increment corresponding to the period between 1920-1940. Accordingly, association module 118C associates mafficking with the time period of 1920-1940.

In this embodiment association module 118C, using threshold value 202 associates mafficking to a particular section of the domain table (i.e. time period of 1920-1940 within the domain table); however, it should be appreciated that in other embodiments, association module 118C may associate a domain table with a received word in its entirety. For example, a word may be associated with a medical frequency domain table, and not just a particular section within the medical frequency domain table.

Figure 3:
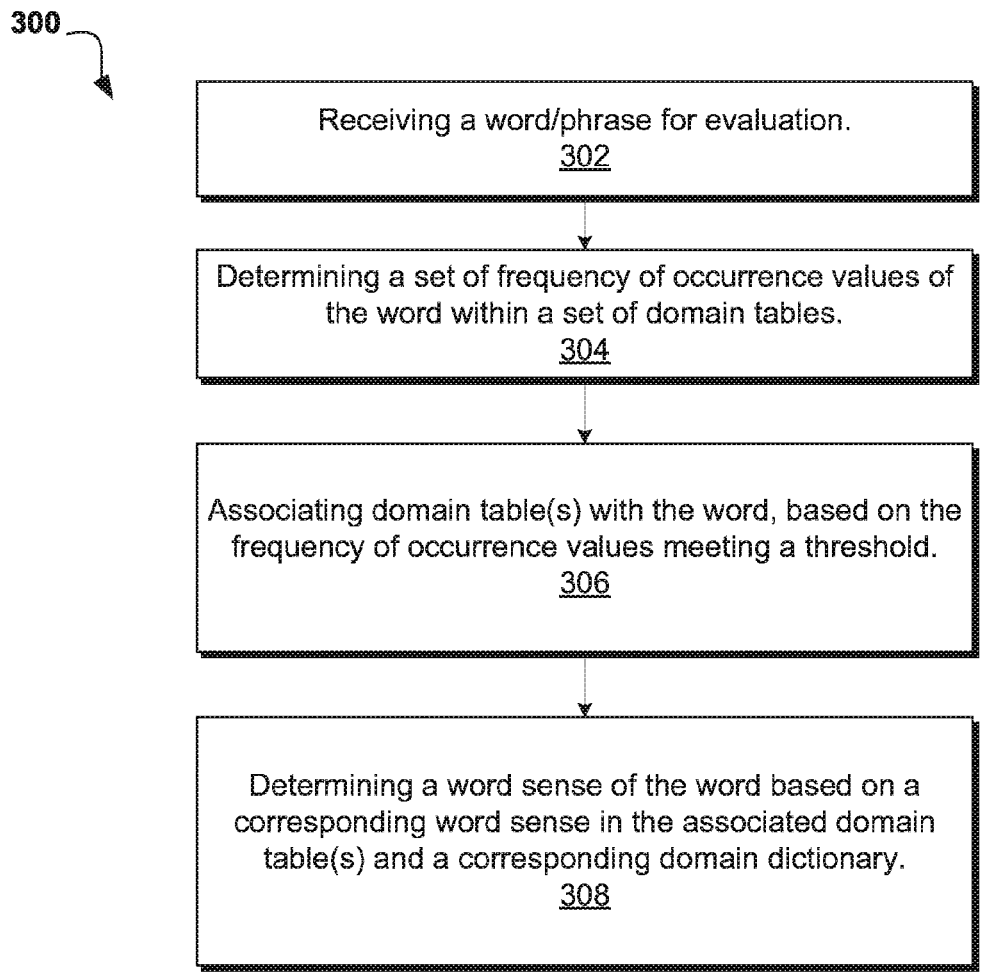
FIG. 3 is a flowchart depicting operational steps of a method for a Domain-based Semantic Analysis Program, in accordance with an embodiment of the present invention.

FIG. 3 is a flowchart depicting operational steps of a method for a Domain-based Semantic Analysis Program 108A and 108B, in accordance with an embodiment of the present invention. In this embodiment, the word necklace from a sentence "patient has an orange necklace" is analyzed. In reference to FIGS. 1, 2, and 3, steps of method 300 may be implemented using one or more modules of a computer program, for example, Domain-based Semantic Analysis Program 108A, and executed by a processor of a computer, such as computer 102. It should be appreciated that FIG. 3 does not imply any limitations with regard to the environments or embodiments which may be implemented. Many modifications to the depicted environment or embodiment shown in FIG. 3 may be made.

At 302, the operation of receiving module 118A is depicted. Receiving module 118A may receive a digital text stream comprising one or more words, and/or corresponding metadata, from an electronic input source. Receiving module 118A may receive the word(s) from a user or a computer implemented system. Non-limiting examples of an input source may be spoken words, typed words, or inputting a corpus electronically from a computer implemented source such as an electronic device (e.g. cell phones or tablets).

In this embodiment, receiving module 118A, receives a sentence ("patient has an orange necklace") from a computer implemented system. For example, receiving module 118A receives the words electronically from an annotation software used by a doctor. Receiving module 118A may receive additional metadata indicating that the domain of the words in the received sentence is medical.

At 304 the operation of determination module 118B is depicted. Determination module 118B may determine a value corresponding to a frequency of occurrence of a received word within a set of one or more domain tables. A domain table comprises one or more arrays of aggregated statistical information about words, within a particular domain, and one or more of corresponding word-senses and/or temporal properties, as described in connection with FIG. 2.

Domain Table(s), in an embodiment, may be pre-loaded into Domain-based Semantic Analysis Program 108A, or retrieved from communication network 110 by Domain-based Semantic Analysis Program 108B. In other embodiments, the domain table(s) could be generated by the user or another computer implemented system. In various embodiments, Domain-based Semantic Analysis Program 108A or 108B may receive domain table(s) or determine a selection of domain table(s) from a user or a computer implemented system. For example, when a user is interested in semantic analysis of a word within a specific time period or semantic analysis of a word within the context of a certain domain, determination module 118B may receive a set of domain table(s) from the user or receive instructions from the user as to which domain table(s) to use. For example, when receiving a word from a computer system, corresponding metadata associated with the received word may be used to determine the selection of domain table(s).

Determination module 118B may also determine a selection of domain table(s) based on previous analysis; Domain-based Semantic Analysis Program 108A or 108B may assign a context value to one or more words within a corpus based on the semantic analysis which Domain-based Semantic Analysis Program 108A or 108B has performed. Determination module 118B may use that context value in order to determine a selection of domain tables when analyzing other words within that corpus. Context value is an indicator which may associate the analyzed word with a context. A non-limiting example of a context value is metadata which may be attached to a word in order to indicate the nature and context of that word. For example, Domain-based Semantic Analysis Program 108A or 108B may analyze a word, within a corpus, and assign an $18^{th}$ century context value to said word (i.e. the determination module 118B determines that the word is from the $18^{th}$ century); when analyzing another word within the same corpus, determination module 118B may determine a selection of domain tables which correspond to $18^{th}$ century based on the $18^{th}$ century context value.

Determination module 118B may also determine the frequency of occurrence of the received word within domain table(s). It should be noted that determining the frequency of occurrence is not the same or exclusive to frequency of occurrence domain tables. Determination module 118B may determine the frequency of occurrence of the received word within a domain table which may be, for example, a frequency of co-occurrence domain table.

In this embodiment, using the metadata received by the receiving module 118A, determination module 118B determines a selection of domain tables(s) based on the medical nature of the word "necklace". Determination module 118B may choose medical frequency domain table, veterinary frequency domain table, temporal frequency domain table, (for example early $20^{th}$ century), medical co-occurrence domain table, veterinary co-occurrence domain table, a word-sense domain table (e.g. a dictionary), and a legal domain table based on the metadata received by receiving module 118A. It should be appreciated that a legal domain table, in this embodiment, may be selected due to a possible legal meaning of some words used in the medical field. Furthermore, in this embodiment, determination module 118B, determines the frequency of occurrence of the word necklace within the above-mentioned domain tables.

At 306, the operation of association module 118C is depicted. Association module 118C may associate one or more domain table(s) with the received word. This association may be based on a value that corresponds to frequency of occurrence of the received word within a domain table meeting a threshold value. For example, if the frequency of occurrence value in a domain table satisfies a threshold value (e.g. the word has been used more times than a threshold value), association module 118C may associate that domain table to the received word.

The threshold value may be predetermined or input by a user. For example, if the user desires a higher threshold value due to the nature of the received word, Domain-based Semantic Analysis Program 108A or 108B may receive an instruction or set of instructions to use a higher threshold. In another example, Domain-based Semantic Analysis Program 108A or 108B may determine a threshold value based on the metadata associated with the received word. For example if the metadata indicates that the word is inherently ambiguous (i.e. pertains to more than one interpretation; having a double meaning) a higher threshold value may be used. A high threshold value corresponds to a high frequency of occurrence within a domain table.

In this embodiment, association module 118C determines a high threshold value based on the metadata which points to the possible medical nature of the word necklace. Association module 118C determines a high threshold, which corresponds to a high degree of certainty (also referred to as a confidence value), because the word is of medical nature and accuracy of word-sense identification may be more important for a medical word than, for example, a word which is predominately used for colloquial purposes.

In this embodiment, association module 118C may associate the word necklace from the sentence "patient has orange necklace" to the medical frequency domain table, veterinary domain table, medical co-occurrence domain table, and veterinary co-occurrence domain table because the word necklace has a high frequency of occurrence within said domain tables; this may be due to high occurrence of the word necklace within the above-mentioned domain tables. For example, the word necklace has a high frequency of occurrence within the medical/veterinary frequency table and a high frequency of co-occurrence with the word patient within the medical/veterinary co-occurrence domain tables (e.g. the word necklace and "patient" co-occur within the same sentence very frequently). Furthermore, in this embodiment, association module 118C does not associate necklace with a domain table which corresponds to early $20^{th}$ century because the frequency of usage of necklace, as determined by the determination module 118B, is not higher than a threshold value with respect to that domain table.

At 308, operation of analyzing module 118D is depicted. Analyzing module 118D may determine a word-sense of the received word based on corresponding word-senses in the associated domain table(s) or a corresponding domain dictionary, or both. Analyzing module 118D may also communicate the one or more word-senses and corresponding confidence values to the user or another computer-implemented system. In an embodiment, analyzing module 118D may search within the associated domain table(s) and semantically analyze the received word based on the corresponding word-sense of the received word in associated domain table(s). In various embodiments, analyzing module 108D may use a domain dictionary which corresponds to the associated domain table determined by the association module 118C. For example if a word satisfies a threshold value and is associated with a "medical co-occurrence domain table", analyzing module may use semantic analysis based on the corresponding word-sense of the received word within the "medical co-occurrence domain table" or a word-sense dictionary which corresponds to the medical terms, or both.

In another embodiment, analyzing module 118D may assign a confidence value to one or more word-sense. The confidence value may be based on the degree of frequency of the word within the associated domain(s), and metadata received by the receiving module 118A. Confidence value may represent the degree of certainty that the word-sense presented by the Domain-based Semantic analysis program 108A and 108B. The higher the confidence value, the higher the possibility of the word-sense being accurate.

Word-senses may be associated with a higher confidence value, if the frequency of occurrence of the word(s) is higher within the associated domain table(s), therefore a higher confidence value may also correspond to a higher threshold value (as explained above). Analyzing module 118D may also assign a word to a confidence value, rank the results based on assigned confidence values, and present multiple word-senses and their corresponding confidence values to the user. For example, the word "admissible" in the sentence "this document is admissible" may be associated with both a legal domain table and a word-sense domain table (e.g. a dictionary) because "admissible" has a high frequency of occurrence in both domain tables and satisfies a threshold. However the corresponding word-senses from these two domain are different. Legal domain table may have a corresponding word-sense such as "tangible evidence that may be introduced to a factfinder" whereas a regular dictionary domain table may have a corresponding word-sense such as "having the right to be admitted to a place". Since determination module 118B may determine that the frequency of occurrence of the word "admissible" within the legal domain table is higher than a word-sense dictionary, analyzing module 118D may assign a higher confidence value to the word-sense from the legal domain table and a lower confidence value to the word-sense from the word-sense domain table.

In this embodiment, analyzing module 118D determines a word-sense of the word necklace within the associated domain tables (associated by the association module 118C). Analyzing module 118D, for example, determines that:

according to the medical co-occurrence domain table, "necklace" has a word-sense of "skin rash encircling the lower neck", when the word necklace has co-occurred with the word "patient" within the same sentence;

according to the medical frequency of occurrence domain table, necklace has a word-sense of "skin rash on the lower neck";

according to the veterinary frequency of occurrence table, necklace has a word-sense of "a band of color across the lower neck";

according to the veterinary frequency of co-occurrence table, necklace has a word-sense of "colors of lower neck" when the word necklace and "patient" have co-occurred;

according to the word-sense domain table, necklace has a meaning of "jewelry".

In this embodiment, analyzing module 118D ranks the domain tables based on confidence value. Based on frequency of occurrence within the associated domain table and metadata received by receiving module 118A, analyzing module 118D assigns a confidence value of 90% to "skin rash encircling the lower neck", 50% to "jewelry" word-sense, and 65% to a "band of color across the lower neck". Analyzing module 118D ranks these domain tables according to their corresponding confidence values and communicates them to the user.

FIG. 4 depicts a block diagram of components a computer system, for example server 112 and computer 102, of distributed computing environment 100 of FIG. 1, in accordance with an embodiment of the present invention.

Server 112 and computer 102 may include one or more processors 402, one or more computer-readable RAMs 404, one or more computer-readable ROMs 406, one or more computer readable storage media 408, device drivers 412, R/W drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 411, are stored on one or more of the computer storage media 408 for execution by one or more of the processors 402 via one or more of the respective RAMs 404 (which typically include cache memory). In the illustrated embodiment, each of the computer readable storage media 408 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Server 112 and computer 102 may also include an R/W drive or interface 414 to read from and write to one or more portable computer readable storage media 426. Application programs 411 on server 112 and computer 102 may be stored on one or more of the portable computer readable storage media 426, read via the respective R/W drive or interface 414 and loaded into the respective computer readable storage media 408.

Sever 112 may also include a network adapter or interface 416, such as a TCP/IP adapter card or wireless communication adapter (such as a 4G wireless communication adapter using OFDMA technology). Application programs 411 on server 112 and may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Server 112 and computer 102 may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, R/W drive or interface 414 and network adapter or interface 416 may comprise hardware and software (stored on computer readable storage media 408 and/or ROM 406).

Based on the foregoing, a computer system, method, and computer program product have been disclosed. However, numerous modifications and substitutions can be made without deviating from the scope of the present invention. Therefore, the present invention has been disclosed by way of example and not limitation.

The invention claimed is:

1. A computer system for identifying word-senses, the computer system comprising:
   one or more computer processors;
   one or more computer-readable storage media;
   program instructions stored on the computer-readable storage media for execution by at least one of the one or more processors, the program instructions comprising:
   program instructions to generate, by a computer, a plurality of arrays of aggregated statistical information of words, their corresponding word-senses, and temporal properties within different professional fields using an n-gram viewer, wherein the aggregated statistical information comprises frequency of usage of words, frequency of occurrence of words, frequency of co-occurrence of words with other words, and their respective corresponding word-senses;
   program instructions to generate, by the computer, a set of domain tables based on the generated plurality of arrays of aggregated statistical information, wherein each of the domain tables within the set of domain tables corresponds to a different professional field comprising medical, veterinary, legal, and engineering;
   program instructions to receive, from a remote server through a network, a digital text stream comprising metadata and one or more words from a doctor, using the computer, the network being an internet connection;
   program instructions to select, using the metadata, a medical frequency domain table, veterinary frequency domain table, and a word-sense domain table from the set of domain tables;
   program instructions to determine a frequency of occurrence value for the received digital text stream within each of the selected domain tables;
   program instructions to receive a threshold from the doctor;
   program instructions to associate the medical frequency domain table with the received digital text stream in response to the frequency of occurrence value satisfying the received threshold;
   program instructions to determine a word-sense of the received digital text stream, by determining a corresponding word sense to the received digital text stream within the medical frequency domain table;
   program instructions to assign a confidence value to the word-sense based on a degree of frequency of occurrence of the received digital text stream within the medical domain, wherein the word-sense has a higher confidence value, when the frequency of occurrence of the received digital text stream is higher within the medical domain table; and
   program instructions to present the word-sense and the confidence value to the doctor.

* * * * *